(12) United States Patent
Kurtz

(10) Patent No.: US 8,596,128 B2
(45) Date of Patent: Dec. 3, 2013

(54) DIRECTED ACOUSTIC SHEAROGRAPHY

(75) Inventor: Russell M. Kurtz, Palos Verdes Estates, CA (US)

(73) Assignee: RAN Science & Technology, LLC, Rolling Hills Estates, CA (US)

(*) Notice: Subject to any disclaimer, the term of this patent is extended or adjusted under 35 U.S.C. 154(b) by 318 days.

(21) Appl. No.: 13/013,057

(22) Filed: Jan. 25, 2011

(65) Prior Publication Data

US 2011/0179874 A1 Jul. 28, 2011

Related U.S. Application Data

(60) Provisional application No. 61/298,335, filed on Jan. 26, 2010.

(51) Int. Cl.
*G01N 29/06* (2006.01)

(52) U.S. Cl.
USPC ............................. 73/643; 356/35.5

(58) Field of Classification Search
USPC .............................. 73/633, 643, 603; 356/35.5
See application file for complete search history.

(56) References Cited

U.S. PATENT DOCUMENTS 4,631,965 A * 12/1986 De Vadder et al. ............. 73/602
5,146,289 A * 9/1992 Newman ..................... 356/35.5

* cited by examiner

*Primary Examiner* — John Chapman, Jr.
(74) *Attorney, Agent, or Firm* — Buchanan Ingersoll & Rooney PC

(57) ABSTRACT

A nondestructive evaluation system, consisting of a metrology device and a directable acoustic transducer, is used to measure the variation of the surface when stress is applied. The directable acoustic transducer selects the location of the applied stress. The difference between the surface during stress application and in the absence of stress detects both surface and buried defects along the location of the stress. By scanning the beam from the acoustic transducer, the location of the stress can be adjusted, enabling the system to locate the detected defect in three dimensions.

8 Claims, 2 Drawing Sheets

DIRECTED ACOUSTIC SHEAROGRAPHY

CROSS-REFERENCE TO RELATED APPLICATION

This application claims priority to U.S. Provisional Patent Application No. 61/298,335 filed Jan. 26, 2010, which is incorporated herein by this reference in its entirety.

BACKGROUND

Modern, complex materials, including (but not limited to) composite and multilayer materials, are prone to defects that cannot be seen from the outside. Some of the most effective methods of detecting these defects are ultrasonic imaging, imaged shearography, and thermal shearography. Ultrasonic imaging is limited by the fact that increasing the frequency of the ultrasonic signal improves imaging resolution, but also reduces the propagation loss. In addition, the higher the ultrasonic frequency, the greater the loss of signal strength when crossing a material boundary. Imaged shearography can produce a high-resolution scan of the material, but its effectiveness decreases rapidly with depth of the defect to be detected. However, many defects are not seen in this technique.

Thermal shearography permits defect detection at greater depth, but the lack of direction in the thermal stress makes it much more difficult to locate the defect that has been detected. In addition, slow propagation of thermal energy makes the detection and location process very slow.

Accordingly, a rapid technique of detecting and localizing buried defects is needed.

SUMMARY

In accordance with an exemplary embodiment, a method of detecting defects in a material, the method comprises: directing an acoustic beam from an acoustic transducer to the material; obtaining a surface profile of the material during a stress application and an absence of stress; and wherein a difference or variation between the surface profile or its derivatives during the stress application and the absence of stress detects a surface and/or a buried defect.

In accordance with another exemplary embodiment, a metrology system for measuring a surface profile of a material, the system comprises: a directable acoustic transducer, which creates an internal stress within the material; and a metrology device, which measures variations of the surface profile or its derivatives created by the directable acoustic transducer.

In accordance with a further exemplary embodiment, a method to determine a difference between a surface profile in a stressed state and an unstressed state, and interpreting the difference in a way that can be used to describe the buried defects, the method comprises: scanning an acoustic beam in angle and in position; and measuring and storing acoustic beam motions of half a beam diameter, wherein an area that is M acoustic beam diameters in length and N in width requires 4×M×N stressed profiles to be taken, for each propagation angle.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION

In accordance with an exemplary embodiment, directed acoustic shearography consists of three components: (1) a method of inducing a localized, directed acoustic beam in the material to be tested; (2) a metrology system for measuring the surface profile or its derivatives of the material to be tested over an area that is large compared to the expected size of the defect; and (3) calculation technology to determine the difference between the surface profile or its derivatives in its stressed and unstressed states, and interpret this difference in a way that can be used to describe the buried defects. It can be appreciated that as set forth herein, surface profile includes the surface profile and it derivatives.

Figure 1:
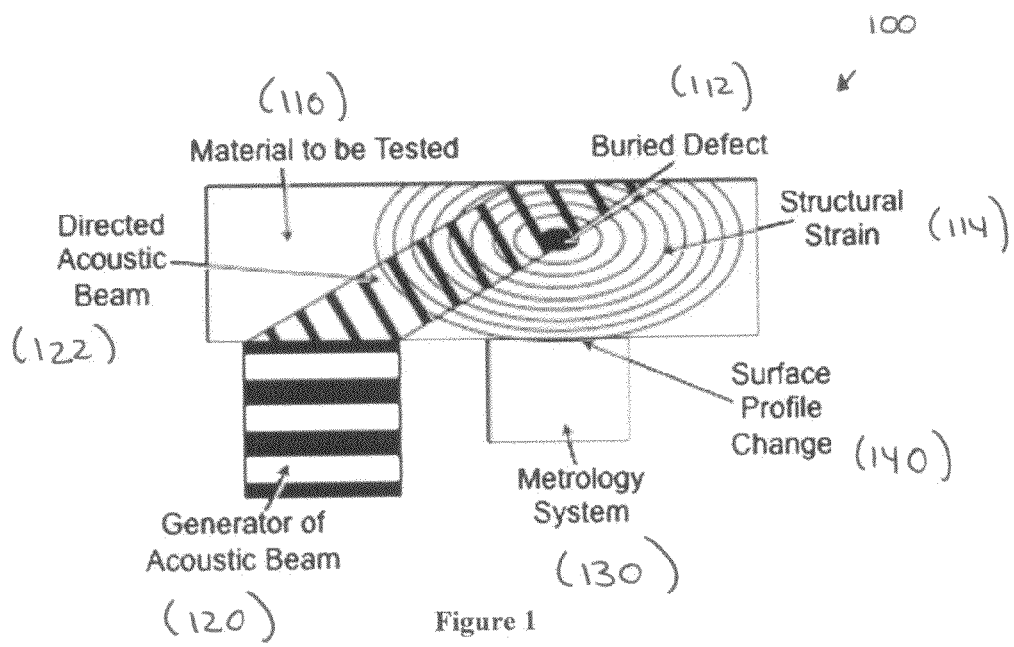
FIG. 1 is a diagram of a system for directed acoustic shearography, which measures the surface profile change induced by a structural strain, which is the response of the material to the interaction of a directed acoustic beam with a buried defect, and wherein the output of the metrology system in this figure goes to a computing system that infers the size and 3D (three-dimensional) location of the defect from the position of the acoustic beam and the surface profile change.

The data-acquisition section of an exemplary device (or system) 100 is shown in FIG. 1. The device (or system) 100 includes a material 110 to be tested having buried defect 112, which causes a structural strain 114 within the material 110. The device 100 also includes a generator of an acoustic beam 120, which produces a directed acoustic beam 122, and a metrology system 130. As shown in FIG. 1, the directed acoustic beam induces a surface profile change 140 on the material 110, which can be measured as more fully set forth below.

Figure 2:
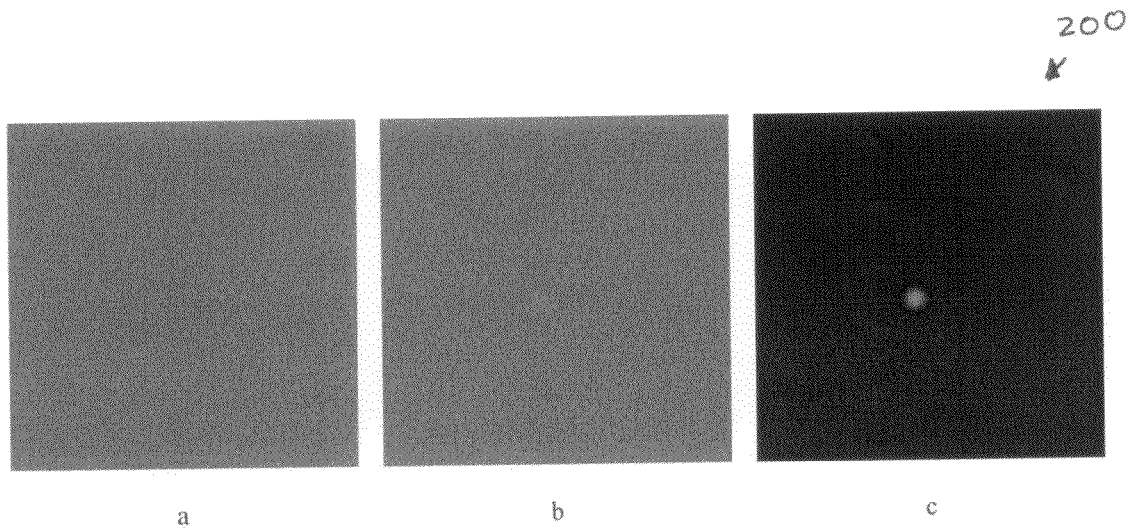
FIG. 2 is a series of diagram showing: (a) a reference image having a flat surface; (b) a stressed image with a small defect, which shows a slightly raised area near the middle; and (c) the difference image, which makes it much easier to determine the surface profile change.

In accordance with an exemplary embodiment, the surface profile of the material 110 to be tested is first measured with no outside stress applied to the system. This is called the reference profile (see FIG. 2a). The directed acoustic beam 122 is then initiated and the surface profile is again measured. This is known as the first stressed profile (see FIG. 2b). The difference between the reference and stressed profiles corresponds to the change in surface profile, which is the input to the calculation routine (see FIG. 2c).

Figure 3:
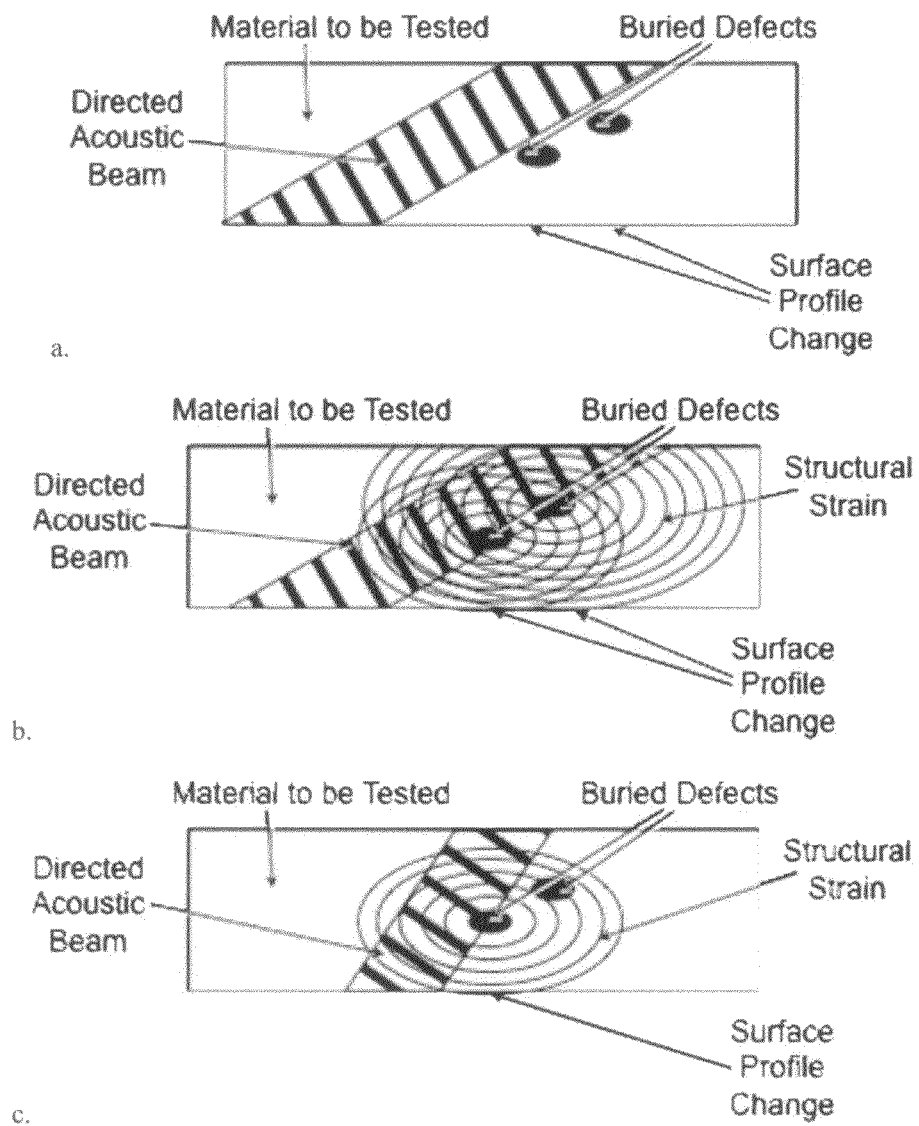
FIG. 3 is a diagram of a directed acoustic beam, which defines the location of induced stress and causes the structural strain leading to a change in the surface profile, and wherein, if the beam does not strike any defect (a), there is no surface profile change; if the beam strikes two defects (b), it will induce two independent surface profile changes, which may or may not overlap; and by rescanning at a different angle (c), the three-dimensional location of each defect can be determined.

In accordance with an exemplary embodiment, and as shown in FIG. 3, the acoustic beam 122 is then rescanned, both in angle and in position. It can be appreciated that at times corresponding to acoustic beam motions of half the beam diameter, the rescanning generates more stressed profiles, which are measured and stored. In accordance with an exemplary embodiment, an area that is M acoustic beam diameters in length and N in width will then require 4×M×N stressed profiles to be taken, for each propagation angle. Measurements at a single propagation angle will be sufficient to locate the defect in two dimensions, one along the length and the other along the width. However, it can be appreciated that by retaking these 4×M×N stressed profiles (4 times M times N) at from two to eight additional propagation angles, sufficient information will be available to locate the defect in all three dimensions.

It can be appreciated that the change in the surface profile is caused by an unbalanced internal stress when the acoustic beam intersects a buried defect. This unbalanced stress produces a structural strain, which propagates to the surface directly above the defect. The strain appears on the surface as a localized change in curvature. This change is detected by subtracting the reference profile from each stressed profile. It can be appreciated that only defects that fall within the acoustic beam will produce changes in the stressed profile, so the position of the defect and its size can be determined from the location and size of the localized curvature change.

In addition, since the unbalanced stress is only dependent on the intensity of the acoustic beam, and not its frequency, the extremely high frequencies used in ultrasonic imaging are not needed. Furthermore, the use of lower acoustic frequencies enables greater measurement depth in the material. In Directed Acoustic Shearography, the low-frequency limit is determined only by the diameter of the acoustic beam as it propagates through the material being tested. This depth, and the Directed Acoustic Shearography capability of detecting the depth of a buried defect through scans at several acoustic beam propagation angles, also provides its superiority to imaged shearography. In addition, the speed at which the acoustic beam propagates through the material provides rapid scanning capability; in aluminum, for example, acoustic energy propagates at approximately 5100 m/s, while thermal energy propagates at approximately 0.003 m/s, so Directed Acoustic Shearography can take measurements at 1,700,000 times the rate of thermal shearography.

In accordance with an exemplary embodiment, the implementation of the above-mentioned system can use a phased array, contact-based acoustic transducer to generate the acoustic beam within the material. For example, the acoustic beam diameter can be 5 mm, which requires the frequency to be at least 500 kHz. The surface metrology system can include a laser interferometer. The difference between the interferometry scans is interpreted as a change in the surface profile, and surface curvature change is determined by the change in the interferometric fringe pattern. This has permitted Directed Acoustic Shearography to detect buried defects whose diameter was 0.75 mm at depths up to 8 mm, with accuracy of 2.5 mm in the length and width directions of the material under test, and 1.5 mm in depth. It can be appreciated that the diameter of the acoustic beam and corresponding frequency can be varied without departing from the spirit and scope of the Direct Acoustic Shearography system as described herein.

It can be appreciated that in accordance with an exemplary embodiment, the system and methods as described herein can be used to measure a device or object, which is embedded in an acoustic couplant or couplants. For example, the acoustic couplant can be water or seawater, wherein the system and methods described herein are used to measure weld integrity in underwater environments.

It will be understood that the foregoing description is of the preferred embodiments, and is, therefore, merely representative of the article and methods of manufacturing the same. It can be appreciated that many variations and modifications of the different embodiments in light of the above teachings will be readily apparent to those skilled in the art. Accordingly, the exemplary embodiments, as well as alternative embodiments, may be made without departing from the spirit and scope of the systems and methods as set forth in the attached claims.

What is claimed is:

1. A method to determine a difference between a surface profile in a stressed state and an unstressed state, and interpreting the difference in a way that can be used to describe the buried defects, the method comprising:
   scanning a localized acoustic beam, in angle and in position;
   measuring and storing acoustic beam motions of half a beam diameter, wherein an area that is M acoustic beam diameters in length and N in width requires 4×M×N stressed profiles to be taken, for each propagation angle;
   interpreting a surface curvature, as calculated from a surface profile, as determining whether or not the acoustic beam has encountered a defect; and
   using the angle and position of the localized acoustic beam to determine a three-dimensional location of buried defects.

2. The method of claim 1, wherein measurements at a single propagation angle will be sufficient to locate the defect in two dimensions, one along the length and the other along the width.

3. The method of claim 2, wherein a 4×M×N stressed profile at from two to eight additional propagation angles is sufficient to locate the defect in three dimensions.

4. The method of claim 3, wherein a device or object being measured is embedded in an acoustic couplant.

5. The method of claim 4, wherein the acoustic couplant is water or seawater.

6. A method to determine a difference between a surface profile in a stressed state and an unstressed state, and interpreting the difference in a way that can be used to describe the buried defects, the method comprising:
   scanning an acoustic beam in angle and in position; and
   measuring and storing acoustic beam motions of half a beam diameter, wherein an area that is M acoustic beam diameters in length and N in width requires 4×M×N stressed profiles to be taken, for each propagation angle, wherein measurements at a single propagation angle will be sufficient to locate the defect in two dimensions, one along the length and the other along the width, and wherein a 4×M×N stressed profile at from two to eight additional propagation angles is sufficient to locate the defect in three dimensions.

7. The method of claim 6, wherein a device or object being measured is embedded in an acoustic couplant.

8. The method of claim 7, wherein the acoustic couplant is water or seawater.

* * * * *